United States Patent [19]

Bernstein

[11] 4,216,164

[45] Aug. 5, 1980

[54] UREIDE INHIBITORS OF CONNECTIVE TISSUE DESTRUCTION

[75] Inventor: Seymour Bernstein, New City, N.Y.

[73] Assignee: American Cyanamid Company, Stamford, Conn.

[21] Appl. No.: 971,174

[22] Filed: Dec. 20, 1978

Related U.S. Application Data

[60] Continuation-in-part of Ser. No. 833,319, Sep. 14, 1977, Pat. No. 4,131,684, which is a division of Ser. No. 684,601, May 10, 1976, abandoned.

[51] Int. Cl.$^2$ .................... C07C 143/48; C07C 69/14
[52] U.S. Cl. ................. 260/506; 260/507 R; 560/251; 424/315; 424/311
[58] Field of Search ................. 260/506, 507; 560/251

[56] References Cited

U.S. PATENT DOCUMENTS

| 1,218,654 | 3/1917 | Heymann et al. | 260/506 |
| 1,218,655 | 3/1917 | Heymann et al. | 260/506 |
| 1,308,071 | 7/1919 | Heymann et al. | 260/506 |
| 2,164,229 | 6/1939 | Coulthard | 260/506 |

Primary Examiner—Nicky Chan
Attorney, Agent, or Firm—Claude J. Caroli

[57] ABSTRACT

Certain ureides of substituted naphtholmonosulfonic acids and salts useful as inhibitors of connective tissue destruction.

9 Claims, No Drawings

UREIDE INHIBITORS OF CONNECTIVE TISSUE DESTRUCTION

CROSS-REFERENCE TO RELATED APPLICATIONS

This application is a continuation-in-part of copending application Ser. No. 833,319, filed Sept. 14, 1977, now U.S. Pat. No. 4,131,684, which in turn is a division of application Ser. No. 684,601, filed May 10, 1976, now abandoned. The amine precursors used to prepare the final products of the present invention form the subject matter of concurrently filed and copending application Ser. No. 971,172. The nitro precursors used to prepare the amine precursors form the subject matter of concurrently filed and copending application Ser. No. 971,173.

BACKGROUND OF THE INVENTION

More specifically, the present invention resides in the concept of certain ureylenebis-[(substituted or unsubstituted-phenylenecarbonylimino)bis-(substituted-naphthalenemon-sulfonic acids)] and salts thereof which are novel compounds useful as inhibitors of connective tissue destruction.

Abnormal destruction of connective tissue by collagenase and/or neutral proteases causes tissue damage and/or tissue dysfunction. In these conditions an inhibitor of connective tissue destruction acting directly or indirectly would be useful in preventing, retarding, or reversing tissue damage and/or collagen diseases.

The term connective tissue refers to a matrix of at least three protein molecules, collagen, proteoglycan and elastin. These molecules play an important role in the structural integrity of normal tissues. Collagen, the most abundant protein in the body occupies a central position in the connective tissue matrix ["*Biochemistry of Collagen*", Ed. G. N. Ramachandran and A. H. Reddi, Academic Press, New York (1976); P. Bornstein, *Ann. Rev. Biochem.*, 43, 567 (1974); J. Fessler and L. Fessler, *Ann. Rev. Biochem.*, 47, 129 (1978)].

Collagen is, for example, the main structural component of the oral tissue (peridontal ligament, alveolar bone, gingiva, and cementum) [Fullmer, et al., *J. Dental Research*, 48, 646 (1969)]. Collagen amounts to 40% of cartilage protein, 90% of bone protein, and over 90% of dry dermis. Articular cartilage is the resilient tissue that covers the articulating extremities in synovial joints. It consists of collagen fibres that are intimately meshed in a hydrated gel of proteoglycan.

Proteoglycan, as it exists in cartilage, is a molecule in which sulfated polysaccharide chains are covalently linked to a protein backbone ["*Dynamics of Connective Tissue Macromolecules*", Ed. P. M. Burleigh and A. R. Poole, North Holland, Amsterdam (1975)].

Elastin is a major connective tissue component of pulmonary structure ["*Elastin and Elastic Tissue*", Ed. L. B. Sandberg, W. R. Gray, and C. Franzblau, Plenum Press, New York (1977)]. The breakdown of elastin of pulmonary connective tissue is considered the primary event in pulmonary emphysema [A. Janoff in "Proteases and Biological Control", *Cold Spring Harbor Conference on Cell Proliferation*, 2, 603 (1975)].

Degradation of fibrous collagen is initiated by a combination of neutral proteases and tissue collagenase as an integral part of a complex immunopathological process which results in the loss of collagen from normal tissue. Under normal conditions cellular mechanisms maintain a careful balance between the rates of collagen synthesis and degradation. However, in certain pathological conditions, the ensuing elevated levels of neutral proteases and collagenase can result in rapid collagen degradation and tissue dysfunction. For example, in periodontal disease, the generated elevated levels of neutral proteases and collagenase in the gingival crevicular fluid rapidly degrade the fibrous collagen supporting the teeth. Periodontal pockets result ultimately from collagen degradation, and as these pockets deepen, support of tooth is lost and alveolar bone is resorbed [K. Ohlsson, I. Ohlsson, and G. I. Basthall, *Acta Odontol. Scand.*, 32, 51 (1974); L. M. Golub, S. Kenneth, H. McEwan, J. B. Curran, and N. S. Ramamurthy, *J. Dental Research*, 55, 177 (1976); L. M. Golub, J. E. Stakin and D. L. Singer, *J. Dental Research*, 53, 1501 (1974); L. M. Wahl, S. M. Wahl, S. E. Mergenhagen, and G. R. Martin, *Proc. Natl. Acad. Sci. U.S.*, 71, 3598 (1974); *Science*, 187, 261 (1975)].

In arthritic conditions such as in rheumatoid arthritis, septic arthritis, and osteoarthritis elevated degradation of collagen and proteoglycan initiate rapid destruction of articular tissue [J. M. Evanson, J. J. Jefferey, and S. M. Krane, *Science*, 158, 499 (1967); E. D. Harris, D. R. Dibona and S. M. Krane, *J. Clin. Invest.*, 48, 2104 (1969); E. D. Harris in *Rheumatoid Arthritis*, Medcom. Press, N.Y. (1974); Z. Werb, C. L. Mainardi, C. A. Vater, and E. D. Harris, *New Eng. J. Med.*, 296, 1017 (1977); J. M. Dayer, R. G. Russell, and S. M. Krane, *Science*, 195, 181 (1977); E. D. Harris, C. A. Vater, C. L. Mainardi, and Z. Werb, *Agents and Actions*, 8, 35 (1978); D. E. Woolley, E. D. Harris, C. L. Mainardi, and C. E. Brinkerhoff, *Science*, 200, 773 (1978); E. D. Harris, C. S. Faulkner, F. E. Brown, *Clin. Orthoped.*, 110, 303 (1975); M. G. Ehrlich, H. J. Mankin, H. Jones, R. Wright, and C. Crisper, *J. Bone Jt. Surg.*, 57A, 565 (1975); S. Gordon, W. Newman, and B. Bloom, *Agents and Action*, 8, 19 (1978); "Mechanisms of Tissue Injury With Reference to Rheumatoid Arthritis", Ed. R. J. Perper, *Ann. N.Y. Acad. Sci.*, 256, 1-450 (1975)].

Increased collagen degradation in bone can result in abnormal bone destruction as in osteoporosis [C. G. Griffith, G. Nichols, J. D. Asher, and B. Flannagan, *J. Am. Med. Assoc.*, 193, 91 (1965); B. Gardner, H. Gray, and G. Hedyati, *Curr. Top. Surg. Res.*, 2, 175 (1970); B. Gardner, S. Wallach, H. Gray, and R. K. Baker, *Surg. Forum*, 22, 435 (1971)]. Collagenase actitity has also resulted in tissue damage in cholesteatoma [M. Abramson, R. W. Schillng, C. C. Huang, and R. G. Salome, *Ann. Otol. Rhinol. Faryngol.*, 81, 158 (1975); M. Abramson and C. C. Huang, *Laryngoscope*, 77, 1 (1976)]. In corneal ulcerations that progress to loss of corneal integrity and function, collagenase has been implicated as a direct factor in corneal destruction [S. I. Brown, C. W. Hook, and N. P. Tragakis, *Invest. Ophthamol.*, 11, 149 (1972); M. B. Berman, C. H. Dohlman, P. F. Davison, and M. Ghadinger, *Exptl. Eye Res.*, 11, 225 (1971)]. Elevated levels of collagenase have also been observed in patients with *epidermolysis bullosa*, and a group of related genetic diseases of the skin [E. A. Bauer, T. G. Dahl, and A. Z. Eisen, *J. Invest. Dermatology*, 68, 119 (1977)].

Increased breakdown of elastin of the lung tissue by neutral proteases (elastase) may contribute to the lesions in pulmonary emphysema [I. Mandel, T. V. Darmle, J. A. Frierer, S. Keller, and G. M. Turino in *Elastin and Elastic Tissue*, Ed. L. B. Sandberg, W. R. Gray, and C. Franzblau, Plenum Press, N.Y., p. 221 (1977)].

A variety of substances, both naturally occurring and synthetically prepared, have been found to be inhibitors of connective tissue destruction, e.g., inhibitors of collagen degradation, that is, as collagenase inhibitors. Such substances include, for example, ethylenediaminetetraacetate, 1,10-phenanthroline, cysteine, dithiothretol and sodium aurio-thiomalate [D. E. Woolley, R. W. Glanville, D. R. Roberts, and J. M. Evanson, Biochem J., 169, 265 (1978); S. Seifter and E. Harper, Chap. 18, "The Collagenases" in The Enzymes (3rd. Edition), 3, 649–697, Ed. by P. D. Boyer, Academic Press, N.Y. (1971)]. In the eye, a number of studies using collagenase inhibitors directly applied to corneal ulcerations have been reported. Calcium ethylenediaminetetraacetate and acetylcysteine reduce the frequency of ulceration in the alkali burned rabbit [M. Berman and C. Dohlman, Arch. Ophthamol., 35, 95 (1975)]. Both cysteine and acetylcysteine have been effective in the treatment of acute and chronic corneal ulceration in the human, although the latter compound was preferred because of its greater stability [S. I. Brown, N. P. Tragakis, and D. B. Pease, Am. J. Ophthalmol., 74, 316 (1972); M. Berman in Trace Components of Plasma: Isolation and Clinical Significance, 7th Annual Red Cross Symposium, p. 225, Alan R. Liss. Inc., N.Y. (1976)].

Naturally occurring collagenase inhibitors include the serum components $\alpha_2$-macroglobulin and $\beta$1-anticollagenase [D. E. Woolley, R. W. Glanville, D. R. Roberts and J. M. Evanson, Biochem. J., 169, 265 (1978)].

While some compounds may inhibit the destructive effect of collagenase on connective tissue by acting directly on collagenase itself, other compounds may inhibit such destruction by coating, binding or competing with sights on the connective tissue in such a manner as to prevent collagenase from attacking it. The present invention, however, is not to be restricted or limited to any particular mechanism or mode of action. Suffice it to say, that the compounds of this invention have utility as inhibitors of connective tissue destruction albeit in whatever manner or mode.

U.S. Pat. No. 2,687,436 discloses substituted 3-(2-naphthyl)-cyclohexanes useful in the treatment of collagen diseases. British Pat. Nos. 856,357 and 1,246,141, disclose 2-aryl-hexahydro-quinolizines and 1-hydroxyl-praline derivatives, respectively, useful for treating diseases affecting connective tissue. The closest known structurally related compound to those of the present invention and disclosed as having collagenase inhibiting activity is found in Thromb. Res. 1977, 10(4), 605–11 wherein the trypanocidal agent trypan blue is reported as inhibiting the activity of collagenase, or a proteinase contaminant in the collagenase preparation. It is interesting, however, that in this same article, the ureide Suramin is reported as not inhibiting the action of collagenase. The closest known ureides to those of the present invention, and not disclosed as inhibitors of connective tissue destruction or as collagenase inhibitors are those ureides found in Journal of the Chemical Society, 3069 (1927), and in U.S. Pat. Nos. 1,218,654 and 1,308,071. The generic disclosure of the U.S. Pat. No. 1,308,071 patent encompasses a vast number of ureides and with proper selection, among the many possible variables, some of the compounds of this invention may be encompassed within this broad generic disclosure. However, such disclosure by itself does not anticipate or render obvious the invention claimed herein.

SUMMARY OF THE INVENTION

This invention is concerned with novel C-substituted naphthalenemonosulfonic ureides which may be represented by Formula I:

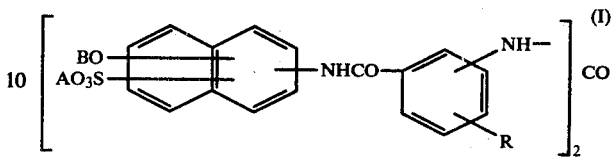

wherein A is hydrogen or a pharmaceutically acceptable salt cation; B is hydrogen, lower ($C_1$–$C_6$) alkanoyl or alkali metal; and R is hydrogen or lower ($C_1$–$C_3$) alkyl.

A preferred form of the present invention is concerned with those ureides wherein neither the R nor the NH-group are ortho to the fixed portion of the carboxamido group (—NHCO—) in the bridgehead and such ureides may be represented by Formulae II, III and IV:

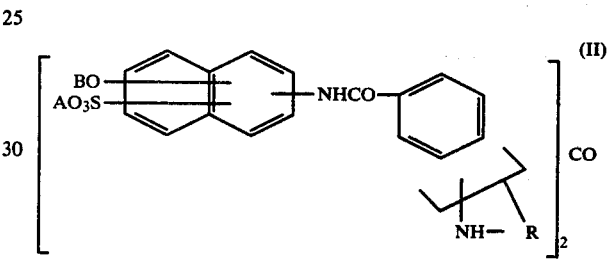

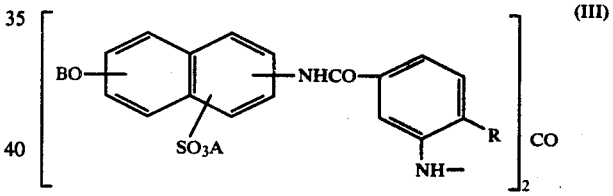

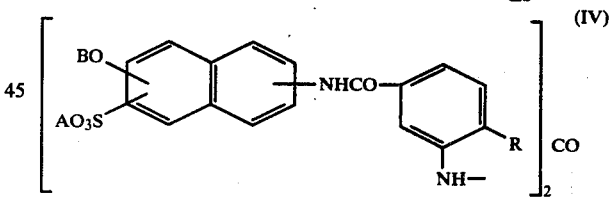

wherein in the above formulae A, B and R are as defined with reference to Formula I.

By pharmacologically acceptable salt cation is meant an alkali metal; an alkaline earth metal; ammonium; primary amine, e.g. ethylamine, secondary amine, e.g., diethylamine or diethanolamine; tertiary amine, e.g., pyridine, triethylamine or 2-dimethylaminomethyldibenzofuran; aliphatic amine, e.g., dicamethylenediamine; or aromatic amine.

Representative compounds encompassed within this invention include, for example, 6,6'-[ureylenebis(m-phenylenecarbonylimino]bis[4-hydroxy-2-naphthalenesulfonic acid]disodium salt; 6,6'-[ureylenebis(p-phenylenecarbonylimino)]bis[4-hydroxy-2-naphthalenesulfonic acid], disodium salt; 6,6'-[ureylenebis[(6-methyl-3,1-phenylenecarbonyl)imino]]bis[4-hydroxy-2-naphthalenesulfonic acid], disodium salt; 6,6'-[ureylenebis[(3-methyl-4,1-phenylenecarbonyl)imino]]- bis[4-hydroxy-2-naphthalenesulfonic acid], disodium salt; 4,4'-[ureylenebis(m-phenylenecarbonylimino)]bis[5-hydroxy-1-naphthalenesulfonic acid], disodium salt; 4,4'-[ureylenebis(p-phenylenecarbonylimino)]bis[5-hydroxy-1-naphthalenesulfonic acid], disodium salt; 4,4'-[ureylenebis[(6-methyl-3,1-phenylenecarbonyl)imino]]bis[5-hydroxy-1-naphthalenesulfonic acid], disodium salt; 4,4'-[ureylenebis[(3-methyl-4,1-phenylenecarbonyl)imino]bis[5-hydroxy-1-naphthalenesulfonic acid], disodium salt; 3,3'-[ureylenebis(m-phenylenecarbonylimino)]bis[4-hydroxy-2-naphthalenesulfonic acid], disodium salt; 3,3'-[ureylenebis(p-phenylenecarbonylimino)]bis[4-hydroxy-2-naphthalenesulfonic acid], disodium salt; 3,3'-[ureylenebis[(6-methyl-3,1-phenylenecarbonyl)imino]]bis[4-hydroxy-2-naphthalenesulfonic acid], disodium salt; 3,3'-[ureylenebis[(3-methyl-4,1-phenylenecarbonyl)imino]]bis[4-hydroxy-2-naphthalenesulfonic acid], disodium salt; 6,6'-[ureylenebis(m-phenylenecarbonylimino)]bis[5-hydroxy-1-naphthalenesulfonic acid], disodium salt; 6,6'-[ureylenebis(p-phenylenecarbonylimino)]bis[5-hydroxy-1-naphthalenesulfonic acid], disodium salt; 6,6'-[ureylenebis[(6-methyl-3,1-phenylenecarbonyl)imino]]bis[5-hydroxy-1-naphthalenesulfonic acid], disodium salt; 6,6'-[ureylenebis[(3-methyl-4,1-phenylenecarbonyl)imino]]bis[5-hydroxy-1-naphthalenesulfonic acid], disodium salt; 3,3'-[ureylenebis(m-phenylenecarbonylimino)]bis[4-hydroxy-1-naphthalenesulfonic acid], disodium salt; 3,3'-[ureylenebis(p-phenylenecarbonylimino)]bis[4-hydroxy-1-naphthalenesulfonic acid], disodium salt; 3,3'-[ureylenebis[(6-methyl-3,1-phenylenecarbonyl)imino]]bis[4-hydroxy-1-naphthalenesulfonic acid], disodium salt; 3,3'-[ureylenebis[(3-methyl-4,1-phenylenecarbonyl)imino]]bis[4-hydroxy-1-naphthalenesulfonic acid], disodium salt; 6,6'-[ureylenebis(m-phenylenecarbonylimino)]bis[5-hydroxy-2-naphthalenesulfonic acid], disodium salt; 6,6'-[ureylenebis(p-phenylenecarbonylimino)]bis[5-hydroxy-2-naphthalenesulfonic acid], disodium salt; 6,6'-[ureylenebis[(6-methyl-3,1-phenylenecarbonyl)imino]]bis[5-hydroxy-2-naphthalenesulfonic acid], disodium salt; 6,6'-[ureylenebis[(3-methyl-4,1-phenylenecarbonyl)imino]]bis[5-hydroxy-2-naphthalenesulfonic acid], disodium salt; 7,7'-[ureylenebis(m-phenylenecarbonylimino)]bis[8-hydroxy-2-naphthalenesulfonic acid], disodium salt; 7,7'-[ureylenebis(p-phenylenecarbonylimino)]bis[8-hydroxy-2-naphthalenesulfonic acid], disodium salt; 7,7'-[ureylenebis[(6-methyl-3,1-phenylenecarbonyl)imino]]bis[8-hydroxy-2-naphthalenesulfonic acid], disodium salt; 7,7'-[ureylenebis[(3-methyl-4,1-phenylenecarbonyl)imino]]bis[8-hydroxy-2-naphthalenesulfonic acid], disodium salt; 7,7'-[ureylenebis(m-phenylenecarbonylimino)]bis[8-hydroxy-1-naphthalenesulfonic acid], disodium salt; 7,7'-[ureylenebis(p-phenylenecarbonylimino)]bis[8-hydroxy-1-naphthalenesulfonic acid], disodium salt; 7,7'-[ureylenebis[(6-methyl-3,1-phenylenecarbonyl)imino]]bis[8-hydroxy-1-naphthalenesulfonic acid]; 7,7'-[ureylenebis[(3-methyl-4,1-phenylenecarbonyl)imino]]bis[8-hydroxy-1-naphthalenesulfonic acid], disodium salt; 7,7'-[ureylenebis(m-phenylenecarbonylimino)]bis[5-hydroxy-1-naphthalenesulfonic acid], disodium salt; 7,7'-[ureylenebis(p-phenylenecarbonylimino)]bis[5-hydroxy-1-naphthalenesulfonic acid], disodium salt; 7,7'-[ureylenebis[(6-methyl-3,1-phenylenecarbonyl)imino]]bis[5-hydroxy-1-naphthalenesulfonic acid], disodium salt; 7,7'-[ureylenebis[(3-methyl-4,1-phenylenecarbonyl)imino]]bis[5-hydroxy-1-naphthalenesulfonic acid], disodium salt; 7,7'-[ureylenebis(m-phenylenecarbonylimino)]bis[5-hydroxy-2-naphthalenesulfonic acid], disodium salt; 7,7'-[ureylenebis(p-phenylenecarbonylimino)]bis[5-hydroxy-2-naphthalenesulfonic acid], disodium salt; 7,7'-[ureylenebis[(6-methyl-3,1-phenylenecarbonyl)imino]]bis[5-hydroxy-2-naphthalenesulfonic acid], disodium salt; 7,7'-[ureylenebis[(3-methyl-4,1-phenylenecarbonyl)imino]]bis[5-hydroxy-2-naphthalenesulfonic acid], disodium salt; 6,6'-[ureylenebis(m-phenylenecarbonylimino)]bis[8-hydroxy-2-naphthalenesulfonic acid], disodium salt; 6,6'-[ureylenebis(m-phenylenecarbonylimino)]bis[8-hydroxy-2-naphthalenesulfonic acid], disodium salt; 6,6'-[ureylenebis[(6-methyl-3,1-phenylenecarbonyl)imino]]bis[8-hydroxy-2-naphthalenesulfonic acid], disodium salt; 6,6'-[ureylenebis[(3-methyl-4,1-phenylenecarbonyl)imino]]bis[8-hydroxy-2-naphthalenesulfonic acid], disodium salt; 4,4'-[ureylenebis(m-phenylenecarbonylimino)]bis[1-hydroxy-2-naphthalenesulfonic acid], disodium salt; 4,4'-[ureylenebis(p-phenylenecarbonylimino)]bis[1-hydroxy-2-naphthalenesulfonic acid], disodium salt; 4,4'-[ureylenebis[(6-methyl-3,1-phenylenecarbonyl)imino]]bis[1-hydroxy-2-naphthalenesulfonic acid], disodium salt; 4,4'-[ureylenebis[(3-methyl-4,1-phenylenecarbonyl)imino]]bis[1-hydroxy-2-naphthalenesulfonic acid], disodium salt; 1,1'-[ureylenebis(m-phenylenecarbonylimino)]bis[4-hydroxy-2-naphthalenesulfonic acid], disodium salt; 1,1'-[ureylenebis(p-phenylenecarbonylimino)]bis[4-hydroxy-2-naphthalenesulfonic acid], disodium salt; 1,1'-[ureylenebis[(6-methyl-3,1-phenylenecarbonyl)imino]]bis[4-hydroxy-2-naphthalenesulfonic acid], disodium salt; 1,1'-[ureylenebis[(3methyl-4,1-phenylenecarbonyl)imino]]bis[4-hydroxy-2-naphthalenesulfonic acid], disodium salt; 8,8'-[ureylenebis(m-phenylenecarbonylimino)]bis[5-hydroxyl-1-naphthalenesulfonic acid], disodium salt; 8,8'-[ureylenebis(p-phenylenecarbonylimino)]bis[5-hydroxy-1-naphthalenesulfonic acid], disodium salt; 8,8'-[ureylenebis[(6-methyl-3,1-phenylenecarbonyl)imino]]bis[5-hydroxy-1-naphthalenesulfonic acid], disodium salt; 8,8'-[ureylenebis[(3-methyl-4,1-phenylenecarbonyl)imino]]bis[5-hydroxyl-1-naphthalenesulfonic acid], disodium salt; 8,8'-[ureylenebis(m-phenylenecarbonylimino)]bis[5-hydroxy-2-naphthalenesulfonic acid], disodium salt; 8,8'-[ureylenebis(p-phenylenecarbonylimino)]bis[5-hydroxy-2-naphthalenesulfonic acid], disodium salt; 8,8'-[ureylenebis[(6-methyl-3,1-phenylenecarbonyl)imino]]bis[5-hydroxy-2-naphthalenesulfonic acid], disodium salt; 8,8'-[ureylenebis[(3-methyl-4,1-phenylenecarbonyl)imino]]bis[5-hydroxy-2-naphthalenesulfonic acid], disodium salt; 5,5'-[ureylenebis(m-phenylenecarbonylimino)]bis[8-hydroxy-2-naphthalenesulfonic acid], disodium salt; 5,5'-[ureylenebis(p-phenylenecarbonylimino)]bis[8-hydroxy-2-naphthalenesulfonic acid], disodium salt; 5,5'-[ureylenebis[(6-methyl-3,1-phenylenecarbonyl)imino]]bis[8-hydroxy-2-naphthalenesulfonic acid], disodium salt; 5,5'-[ureylenebis[(3-methyl-4,1-phenylenecarbonyl)imino]]bis[8-hydroxy-2-naphthalenesulfonic acid], disodium salt; 5,5'-[ureylenebis(m-phenylenecarbonylimino)]bis[8-hydroxy-1-naphthalenesulfonic acid], disodium salt; 5,5'-[ureylenebis(p-phenylenecarbonylimino)]bis[8-hydroxy-1-naphthalenesulfonic acid], disodium salt; 5,5'-[ureylenebis[(6-methyl-3,1-phenylenecarbonyl)imino]]bis[8-hydroxy-1-naphthalenesulfonic acid], disodium salt; 5,5'-[ureylenebis[(3-methyl-4,1-phenylenecarbonyl)imino]]bis[8-hydroxy-1-naphthalenesulfonic acid], disodium salt; 5,5'-[ureylenebis(m-phenylenecarbonylimino)]bis[1-hydroxy-2-naphthalenesulfonic acid], disodium salt; 5,5'-[ureylenebis(p-phenylenecarbonylimino)]bis[1-hydroxy-2-naphthalenesulfonic acid], disodium salt; 5,5'-[ureylenebis[(6-methyl-3,1-phenylenecarbonyl)imino]]bis[1-hydroxy-2-naphthalenesulfonic acid], disodium salt; 5,5'-[ureylenebis[(3-methyl-4,1-phenylenecarbonyl)imino]]bis[1-hydroxy-2-naphthalenesulfonic acid], disodium salt; 8,8'-[ureylenebis(m-phenylenecarbonylimino)]bis[4-hydroxy-2-naphthalenesulfonic acid], disodium salt; 8,8'-[ureylenebis(p-phenylenecarbonylimino)]bis[4-hydroxy-2-naphthalenesulfonic acid], disodium salt; 8,8'-[ureylenebis[(6-methyl-3,1-phenylenecarbonyl)imino]]bis[4-hydroxy-2-naphthalenesulfonic acid], disodium salt; 8,8'-[ureylenebis[(3-methyl-4,1-phenylenecarbonyl)imino]]bis[4-hydroxy-2-naphthalenesulfonic acid], disodium salt; 8,8'-[ureylenebis(m-phenylenecarbonylimino)]bis[4-hydroxy-1-naphthalenesulfonic acid], disodium salt; 8,8'-[ureylenebis(p-phenylenecarbonylimino)]bis[4-hydroxy-1-naphthalenesulfonic acid], disodium salt; 8,8'-[ureylenebis[(6-methyl-3,1-phenylenecarbonyl)imino]]bis[4-hydroxy-1-naphthalenesulfonic acid], disodium salt; 8,8'-[ureylenebis[(3-methyl-4,1-phenylenecarbonyl)imino]]bis[4-hydroxy-1-naphthalenesulfonic acid], disodium salt; 1,1'-[ureylenebis(m-phenylenecarbonylimino)]bis[5-hydroxy-2-naphthalenesulfonic acid], disodium salt; 1,1'-[ureylenebis(p-phenylenecarbonylimino)]bis[5-hydroxy-2-naphthalenesulfonic acid], disodium salt; 1,1'-[ureylenebis[(6-methyl-3,1-phenylenecarbonyl)imino]]bis[5-hydroxy-2-naphthalenesulfonyl acid], disodium salt; 1,1'-[ureylenebis[(3-methyl-4,1-phenylenecarbonyl)imino]]bis[5-hydroxy-2-naphthalenesulfonic acid], disodium salt; 4,4'-[ureylenebis(m-phenylenecarbonylimino)]bis[8-hydroxy-1-naphthalenesulfonic acid], disodium salt; 4,4'-[ureylenebis(p-phenylenecarbonylimino)]bis[8-hydroxy-1-naphthalenesulfonic acid], disodium salt; 4,4'-[ureylenebis[(6-methyl-3,1-phenylenecarbonyl)imino]]bis[8-hydroxy-1-naphthalenesulfonic acid], disodium salt; 4,4'-[ureylenebis[(3-methyl-4,1-phenylenecarbonyl)imino]]bis[8-hydroxy-1-naphthalenesulfonic acid], disodium salt; 6,6'-[ureylenebis(m-phenylenecarbonylimino)]bis[1-hydroxy-2-naphthalenesulfonic acid], disodium salt; 6,6'-[ureylenebis(p-phenylenecarbonylimino)]bis[1-hydroxy-2-naphthalenesulfonic acid], disodium salt; 6,6'-[ureylenebis[(6-methyl-3,1-phenylenecarbonyl)imino]]bis[1-hydroxy-2-naphthalenesulfonic acid], disodium salt; 6,6'-[ureylenebis[(3-methyl-4,1-phenylenecarbonyl)imino]]bis[1-hydroxy-2-naphthalenesulfonic acid], disodium salt; 7,7'-[ureylenebis(m-phenylenecarbonylimino)]bis[4-hydroxy-2-naphthalenesulfonic acid], disodium salt; 7,7'-[ureylenebis(p-phenylenecarbonylimino)]bis[4-hydroxy-2-naphthalenesulfonic acid], disodium salt; 7,7'-[ureylenebis[(6-methyl-3,1-phenylenecarbonyl)imino]]bis[4-hydroxy-2-naphthalenesulfonic acid], disodium salt; 7,7'-[ureylenebis[(3-methyl-4,1-phenylenecarbonyl)imino]]bis[4-hydroxy-2-naphthalenesulfonic acid], disodium salt; 7,7'[ureylenebis(m-phenylenecarbonylimino)]bis[4-hydroxy-1-naphthalenesulfonic acid], disodium salt; 7,7'-[ureylenebis(p-phenylenecarbonylimino)]bis[4-hydroxy-1-naphthalenesulfonic acid], disodium salt; 7,7'-[ureylenebis[(6-methyl-3,1-phenylenecarbonyl)imino]]bis[4-hydroxy-1-naphthalenesulfonic acid], disodium salt; 7,7'-[ureylenebis[(3-methyl-4,1-phenylenecarbonyl)imino]]bis[4-hydroxy-1-naphthalenesulfonic acid], disodium salt; 2,2'-[ureylenebis(m-phenylenecarbonylimino)]bis[5-hydroxy-1-naphthalenesulfonic acid], disodium salt; 2,2'-[ureylenebis(p-phenylenecarbonylimino)]bis[5-hydroxy-1-naphthalenesulfonic acid], disodium salt; 2,2'-[ureylenebis][(6-methyl-3,1-phenylenecarbonyl)imino]]bis[5-hydroxy-1-naphthalenesulfonic acid], disodium salt; 2,2'-[ureylenebis[(3-methyl-4,1-phenylenecarbonyl)imino]]bis[5-hydroxy-1-naphthalenesulfonic acid], disodium salt; 8,8'-[ureylenebis(m-phenylenecarbonylimino)]bis[1-hydroxy-2-naphthalenesulfonic acid], disodium salt; 8,8'-[ureylenebis(p-phenylenecarbonylimino)]bis[1-hydroxy-2-naphthalenesulfonic acid], disodium salt; 8,8'-[ureylenebis[(6-methyl-3,1-phenylenecarbonyl)imino]]bis[1-hydroxy-2-naphthalenesulfonic acid], disodium salt; 8,8'-[ureylenebis[(3-methyl-4,1-phenylenecarbonyl)imino]]bis[1-hydroxy-2-naphthalenesulfonic acid], disodium salt; 5,5'-[ureylenebis(m-phenylenecarbonylimino)]bis[4-hydroxy-2-naphthalenesulfonic acid], disodium salt; 5,5'-[ureylenebis(p-phenylenecarbonylimino)]bis[4-hydroxy-2-naphthalenesulfonic acid], disodium salt; 5,5'-[ureylenebis[(6-methyl-3,1-phenylenecarbonyl)imino]]bis[4-hydroxy-2-naphthalenesulfonic acid], disodium salt; 5,5'-[ureylenebis[(3-methyl-4,1-phenylenecarbonyl)imino]]bis[4-hydroxy-2-naphthalenesulfonic acid], disodium salt; 5,5'-[ureylenebis(m-phenylenecarbonylimino)]bis[4-hydroxy-1-naphthalenesulfonic acid], disodium salt; 5,5'-[ureylenebis(p-phenylenecarbonylimino)]bis[4-hydroxy-1-naphthalenesulfonic acid], disodium salt; 5,5'-[ureylenebis[(6-methyl-3,1-phenylenecarbonyl)imino]]bis[4-hydroxy-1-naphthalenesulfonic acid], disodium salt; 5,5'-[ureylenebis[(3-methyl-4,1-phenylenecarbonyl)imino]]bis[4-hydroxy-1-naphthalenesulfonic acid], disodium salt; 4,4'-[ureylenebis(m-phenylenecarbonylamino)]bis[5-hydroxy-2-naphthalenesulfonic acid], disodium salt; 4,4'-[ureylenebis(p-phenylenecarbonylimino)]bis[5-hydroxy-2-naphthalenesulfonic acid], disodium salt; 4,4'-[ureylenebis[(6-methyl-3,1-phenylenecarbonyl)imino]]bis[5-hydroxy-2-naphthalenesulfonic acid], disodium salt; 4,4'-[ureylenebis[(3-methyl-4,1-phenylenecarbonyl)imino]]bis[5-hydroxy-2-naphthalenesulfonic acid], disodium salt; 1,1-[ureylenebis(m-phenylenecarbonylimino)]bis[-hydroxy-2-naphthalenesulfonic acid], disodium salt; 1,1'-[ureylenebis(p-phenylenecarbonylimino)]bis[8-hydroxy-2-naphthalenesulfonic acid], disodium salt; 1,1'-[ureylenebis[(6-methyl-3,1-phenylenecarbonyl)imino]]bis[8-hydroxy-2-naphthalenesulfonic acid], disodium salt; 1,1'-[ureylenebis[(3-methyl-4,1-phenylenecarbonyl)imino]]bis[8-hydroxy-2-naphthalenesulfonic acid], disodium salt; 4,4'-[ureylenebis(m-phenylenecarbonylimino)]bis[3-hydroxy-2-naphthalenesulfonic acid], disodium salt; 4,4'-[ureylenebis(p-phenylenecarbonylimino)]bis[3-hydroxy-2-naphthalenesulfonic acid], disodium salt; 4,4'-[ureylenebis[(6-methyl-3,1-phenylenecarbonyl)imino]]bis[3-hydroxy-2-naphthalenesulfonic acid], disodium salt; 4,4'-[ureylenebis[(3-methyl-4,1-phenylenecarbonyl)imino]]bis[3-hydroxy-2-naphthalenesulfonic acid], disodium salt; 4,4'-[ureylenebis(m-phenylenecarbonylimino)]bis[3-hydroxy-1-naphthalenesulfonic acid], disodium salt; 4,4'-[ureylenebis(p-phenylenecarbonylimino)]bis[3-hydroxy-1-naphthalenesulfonic acid[, disodium salt; 4,4'-[ureylenebis[(6-methyl-3,1-phenylenecarbonyl)imino]]bis[3-hydroxy-1-naphthalenesulfonic acid], disodium salt; 4,4'-[ureylenebis[(3-methyl-4,1-phenylenecarbonyl)imino]]bis[3-hydroxy-1-naphthalenesulfonic acid], disodium salt; 5,5'-[ureylenebis(m-phenylenecarbonylimino)]bis[6-hydroxy-1-naphthalenesulfonic acid], disodium salt; 5,5'-[ureylenebis(p-phenylenecarbonylimino)]bis[6-hydroxy-1-naphthalenesulfonic acid], disodium salt; 5,5'-[ureylenebis[(6-methyl-3,1-phenylenecarbonyl)imino]]bis[6-hydroxy-1-naphthalenesulfonic acid], disodium salt; 5,5'-[ureylenebis[(3-methyl-4,1-phenylenecarbonyl)imino]]bis[6-hydroxy-1-naphthalenesulfonic acid], disodium salt; 5,5'-[ureylenebis(m-phenylenecarbonylimino)]bis[6-hydroxy-2-naphthalenesulfonic acid], disodium salt; 5,5'-[ureylenebis(p-phenylenecarbonylimino)]bis[6-hydroxy-2-naphthalenesulfonic acid], disodium salt; 5,5'-[ureylenebis[(6-methyl-3,1-phenylenecarbonyl)imino]]bis[6-hydroxy-2-naphthalenesulfonic acid], disodium salt; 5,5'-[ureylenebis[(3-methyl-4,1-phenylenecarbonyl)imino]]bis[6-hydroxy-2-naphthalenesulfonic acid], disodium salt; 8,8'-[ureylenebis(m-phenylenecarbonylimino)]bis[7-hydroxy-2-naphthalenesulfonic acid], disodium salt; 8,8'-[ureylenebis(p-phenylenecarbonylamino)]bis[7-hydroxy-2-naphthalenesulfonic acid], disodium salt; 8,8'-[ureylenebis[(6-methyl-3,1-phenylenecarbonyl)imino]]bis[7-hydroxy-2-naphthalenesulfonic acid], disodium salt; 8,8'-[ureylenebis[(3-methyl-4,1-phenylenecarbonyl)imino]]bis[7-hydroxy-2-naphthalenesulfonic acid], disodium salt; 8,8'-[ureylenebis[m-phenylenecarbonylimino)]bis[7-hydroxy-1-naphthalenesulfonic acid], disodium salt; 8,8'-[ureylenebis(p-phenylenecarbonylamino)]bis[7-hydroxy-1-naphthalenesulfonic acid], disodium salt; 8,8'-[ureylenebis[(6-methyl-3,1-phenylenecarbonyl)imino]]bis[7-hydroxy-1-naphthalenesulfonic acid], disodium salt; 8,8'-[ureylenebis[(3-methyl-4,1-phenylenecarbonyl)imino]]bis[7-hydroxy-1-naphthalenesulfonic acid], disodium salt; 6,6'-[ureylenebis(m-phenylenecarbonylimino)]bis[7-hydroxy-2-naphthalenesulfonic acid], disodium salt; 6,6'-[ureylenebis(p-phenylenecarbonylimino)]bis[7-hydroxy-2-naphthalenesulfonic acid], disodium salt; 6,6'-[ureylenebis[(6-methyl-3,1-phenylenecarbonyl)imino]]bis[7-hydroxy-2-naphthalenesulfonic acid], disodium salt; 6,6'-[ureylenebis[(3-methyl-4,1-phenylenecarbonyl)imino]]bis[7-hydroxy-2-naphthalenesulfonic acid], disodium salt; 4,4'-[ureylenebis(m-phenylenecarbonylimino)]bis[2-hydroxy-1-naphthalenesulfonic acid], disodium salt; 4,4'-[ureylenebis(p-phenylenecarbonylimino)]bis[2-hydroxy-1-naphthalenesulfonic acid], disodium salt; 4,4'-[ureylenebis[(6-methyl-3,1-phenyllenecarbonyl)imino]]bis[2-hydroxy-1-naphthalenesulfonic acid], disodium salt; 4,4'-[ureylenebis[(3-methyl-4,1-phenylenecarbonyl)imino]]bis[2-hydroxy-1-naphthalenesulfonic acid], disodium salt; 8,8'-[ureylenebis(m-phenylenecarbonylimino)]bis[3-hydroxy-1-naphthalenesulfonic acid], disodium salt; 8,8'-[ureylenebis(p-phenylenecarbonylimino)]bis[3-hydroxy-1-naphthalenesulfonic acid], disodium salt; 8,8'-[ureylenebis[(6-methyl-3,1-phenylenecarbonyl)imino]]bis[3-hydroxyl-naphthalenesulfonic acid], disodium salt; 8,8'-[ureylenebis[(3-methyl-4,1-phenylenecarbonyl)imino]]bis[3-hydroxy-1-naphthalenesulfonic acid], disodium salt; 5,5'-[ureylenebis(m-phenylenecarbonylimino)]bis[7-hydroxy-2-naphthalenesulfonic acid], disodium salt; 5,5'-[ureylenebis(p-phenylenecarbonylimino)]bis[7-hydroxy-1-naphthalenesulfonic acid], disodium salt; 5,5'-[ureylenebis[(6-methyl-3,1-phenylenecarbonyl)imino]]bis[7-hydroxy-2-naphthalenesulfonic acid], disodium salt; 5,5'-[ureylenebis[(3-methyl-4,1-phenylenecarbonyl)imino]]bis[7-hydroxy-2-naphthalenesulfonic acid], disodium salt; 4,4'-[ureylenebis(m-phenylenecarbonylimino)]bis[7-hydroxy-2-naphthalenesulfonic acid], disodium salt; 4,4'-[ureylenebis(p-phenylenecarbonylimino)]bis[7-hydroxy-2-naphthalenesulfonic acid], disodium salt; 4,4'-[ureylenebis[(6-methyl-3,1-phenylenecarbonyl)imino]]bis[7-hydroxy-2-naphthalenesulfonic acid], disodium salt; 4,4'-[ureylenebis[(3-methyl-4,1-phenylenecarbonyl)imino]]bis[7-hydroxy-2-naphthalenesulfonic acid], disodium salt; 4,4'-[ureylenebis(m-phenylenecarbonylimino)]bis[7-hydroxy-1-naphthalenesulfonic acid], disodium salt; 4,4'-[ureylenebis(p-phenylenecarbonylimino)]bis[7-hydroxy-1-naphthalenesulfonic acid], disodium salt; 4,4'-ureylenebis[(6-methyl-3,1-phenylenecarbonyl)imino]]bis[7-hydroxy-1-naphthalenesulfonic acid], disodium salt; 4,4'-[ureylenebis[(3-methyl-4,1-phenylenecarbonyl)imino]]bis[7-hydroxy-1-naphthalenesulfonic acid], disodium salt; 7,7'-[ureylenebis(m-phenylenecarbonylimino)]bis[3-hydroxy-1-naphthalenesulfonic acid], disodium salt; 7,7'-[ureylenebis(p-phenylenecarbonylimino)]bis[3-hydroxy-1-naphthalenesulfonic acid], disodium salt; 7,7'-[ureylenebis[6-methyl-3,1-phenylenecarbonyl)imino]]bis[3-hydroxy-1-naphthalenesulfonic acid], disodium salt; 7,7'-[ureylenebis[(3-methyl-4,1-phenylenecarbonyl)imino]]bis[3-hydroxy-1-naphthalenesulfonic acid], disodium salt; 3,3'-[ureylenebis(m-phenylenecarbonylimino)]bis[7-hydroxy-1-naphthalenesulfonic acid], disodium salt; 3,3'-[ureylenebis(p-phenylenecarbonylimino)]bis[7-hydroxy-1-naphthalenesulfonic acid], disodium salt; 3,3'-[ureylenebis[(6-methyl-3,1-phenylenecarbonyl)imino]]bis[7-hydroxy-1-naphthalenesulfonic acid], disodium salt; 3,3'-[ureylenebis[(3-methyl-4,1-phenylenecarbonyl)imino]]bis[7-hydroxy-1-naphthalenesulfonic acid], disodium salt; 6,6'-[ureylenebis(m-phenylenecarbonylimino)bis[3-hydroxy-2-naphthalenesulfonic acid], disodium salt; 6,6'-[ureylenebis(p-phenylenecarbonylimino)]bis[3-hydroxy-2-naphthalenesulfonic acid], disodium salt; 6,6'-[ureylenebis[(6-methyl-3,1-phenylenecarbonyl)imino]]bis[3-hydroxy-2-naphthalenesulfonic acid], disodium salt; 6,6'-[ureylenebis[(3-methyl-4,1-phenylenecarbonyl)imino]]bis[3-hydroxy-2-naphthalenesulfonic acid], disodium salt; 3,3'-[ureylenebis(m-phenylenecarbonylimino)]6-hydroxy-2-naphthalenesulfonic acid], disodium salt; 3,3'-[ureylenebis(p-phenylenecarbonylimino)]bis[6-hydroxy-2-naphthalenesulfonic acid], disodium salt; 3,3'-[ureylenebis[(6-methyl-3,1-phenylenecarbonyl)imino]]bis[6-hydroxy-2-naphthalenesulfonic acid], disodium salt; 3,3'-[ureylenebis[(3-methyl-4,1-phenylenecarbonyl)imino]]bis[6-hydroxy-2-naphthalenesulfonic acid], disodium salt; 4,4'-[ureylenebis(m-phenylenecarbonylimino)]bis[6-hydroxy-1-naphthalenesulfonic acid], disodium salt; 4,4'-[ureylenebis(p-phenylenecarbonylimino)]bis[6-hydroxy-1-naphthalenesulfonic acid], disodium salt; 4,4'-[ureylenebis[(6-methyl-3,1-phenylenecarbonyl)imino]]bis[6-hydroxy-1-naphthalenesulfonic acid], disodium salt; 4,4'-[ureylenebis[(3-methyl-4,1-phenylenecarbonyl)imino]]bis[6-hydroxy-1-naphthalenesulfonic acid], disodium salt; 5,5'-[ureylenebis(m-phenylenecarbonylimino)]bis[3-hydroxy-1-naphthalenesulfonic acid], disodium salt; 5,5'-[ureylenebis(p-phenylenecarbonylimino)]bis[3-hydroxy-1-naphthalenesulfonic acid], disodium salt; 5,5'-[ureylenebis[(6-methyl-3,1-phenylenecarbonyl)imino]]bis[3-hydroxy-1-naphthalenesulfonic acid], disodium salt; 5,5'-[ureylenebis[(3-methyl-4,1-phenylenecarbonyl)imino]]bis[3-hydroxy-1-naphthalenesulfonic acid], disodium salt; 4,4'-[ureylenebis(m-phenylenecarbonylimino)]bis[6-hydroxy-2-naphthalenesulfonic acid], disodium salt; 4,4'-[ureylenebis(p-phenylenecarbonylimino)]bis[6-hydroxy-2-naphthalenesulfonic acid], disodium salt; 4,4'-[ureylenebis[(6-methyl-3,1-phenylenecarbonyl)imino]]bis[6-hydroxy-2-naphthalenesulfonic acid], disodium salt; 4,4'-[ureylenebis[(3-methyl-4,1-phenylenecarbonyl)imino]]bis[6-hydroxy-2-naphthalenesulfonic acid], disodium salt; 4,4'-[ureylenebis(m-phenylenecarbonylimino)]bis[3-hydroxy-1-naphthalenesulfonic acid], diacetate (diester); 4,4'-[ureylenebis(p-phenylenecarbonylimino)]bis[3-hydroxy-1-naphthalenesulfonic acid], diacetate (diester); 4,4'-[ureylenebis[(6-methyl-3,1-phenylenecarbonyl)imino]]bis[3-hydroxy-1-naphthalenesulfonic acid], diacetate (diester); 4,4'-[ureylenebis[(3-methyl-4,1-phenylenecarbonyl)imino]]bis[3-hydroxy-1-naphthalenesulfonic acid], diacetate (diester); 6,6'-[ureylenebis(p-phenylenecarbonylimino)]bis[4-hydroxy-2-naphthalenesulfonic acid]tetrasodium salt; 6,6'-[ureylenebis(m-phenylenecarbonylimino)]bis[4-hydroxy-2-naphthalenesulfonic acid]tetrasodium salt; 6,6'-[ureylenebis(4-methyl-3,1-phenylene)carbonylimino]bis[4-hydroxy-2-naphthalenesulfonic acid]disodium salt; and 6,6'-[ureylenebis(3-methyl-4,1-phenylene)carbonylimino]-bis(4-hydroxy-2-naphthalenesulfonic acid]disodium salt.

This invention is also concerned with a method of inhibiting connective tissue destruction in a warm-blooded animal which comprises administering to said animal an effective inhibiting amount of a compound encompassed within Formulae I, II, III or IV. Moreover, this invention is concerned with a method of inhibiting the degradation sequelae of collagenase activity in a body fluid, such as crevicular fluid, synovial fluid and the like, which comprises subjecting body fluid collagenase to the action of an effective collagenase inhibiting amount of a compound encompassed within the above formulae. Body fluid can include blood, plasma, serum, synovial fluid, crevicular fluid, ocular fluid, etc., containing collagenase. The method of use aspect of this invention is further concerned with a method of inhibiting the action of collagenase in a warm-blooded animal which comprises internally administering to said animal an effective collagenase inhibiting amount of a compound encompassed with the above formulae.

Since the compounds of the present invention find utility as inhibitors of connective tissue destruction or as collagenase inhibitors in body fluids, as such they may be useful in ameliorating or preventing those pathological reactions resulting from the functioning of collagenase, and in the therapeutic treatment of warm-blooded animals having connective tissue disorders such as periodontal diseases and diseases of the teeth, osteoporosis, osteolysis, Paget's disease, hyperparathyroidism of renal failure, rheumatoid arthritis, septic arthritis, osteoarthritis, gout, acute synovitis, scleroderma, psoriasis, epidermolysis bullosa, keloids, blisters, cholesteatoma of the ear, and corneal ulceration. The compounds of the present invention may also be useful in those pathological states where excessive activity of neutral proteases causes tissue damage.

The compounds of the present invention may be prepared according to the following Flowchart A.

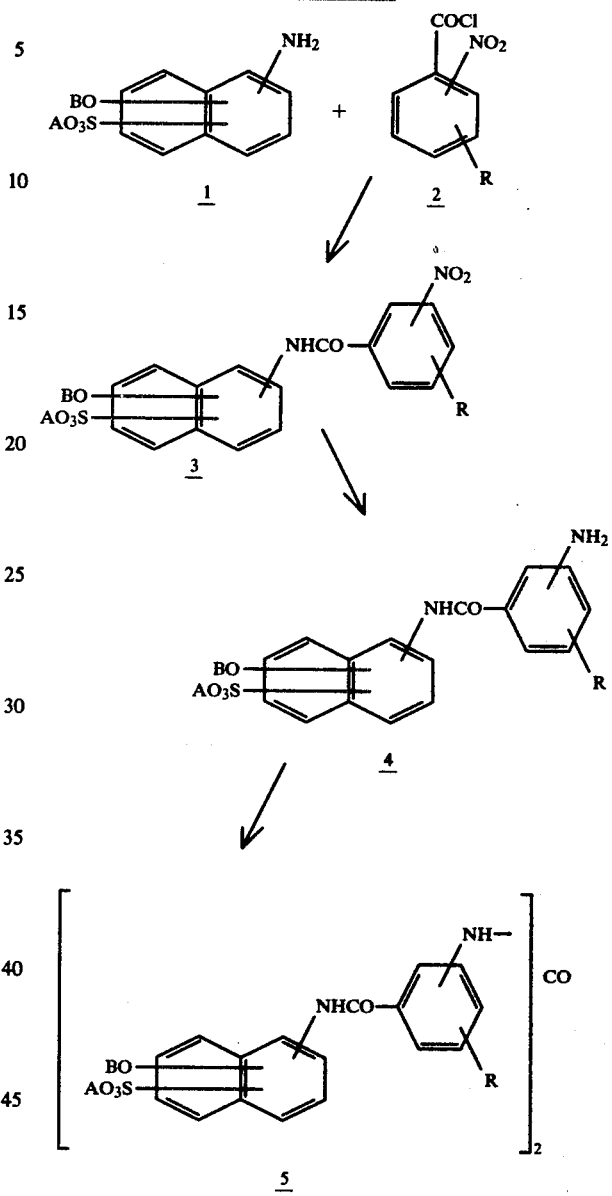

With reference to Flowchart A, a substituted-aminonaphthalenemonosulfonic acid 1 is dissolved in water, made basic with any suitable base such as, for example, an alkali acetate or alkali metal carbonate, reacted with an alkali acetate such as sodium acetate, filtered and reacted under an inert atmosphere, e.g., nitrogen, with an excess substituted nitrobenzoyl chloride 2, giving a substituted nitrobenzamido-substituted-naphthalenesulfonic acid 3. This nitro derivative 3 is then hydrogenated in the presence of a suitable catalyst, giving the corresponding amine derivative 4. The amine 4 is dissolved in a basic solution of pyridine and water and then phosgenated. The final ureide product 5 is extracted from conventional organic solvents such as ethanol or ether. The resulting compound may be converted to its salt in a known manner.

DETAILED DESCRIPTION OF THE INVENTION

The following will serve to illustrate the invention in more detail.

EXAMPLE 1

Amine Precursor
6-(m-aminobenzamido)-4-hydroxy-2-naphthalenesulfonic acid

A suspension of 180 g. of 6-amino-4-hydroxy-2-naphthalenesulfonic acid in 1800 ml. of water is adjusted to pH 7.2–7.5 with aqueous sodium hydroxide solution. The solution is filtered and to the filtrate is added 181.8 g. of sodium acetate trihydrate, followed by 190.8 g. of m-nitrobenzoyl chloride. The mixture is stirred vigorously under nitrogen at room temperature for 8 hours and then filtered. The solid is washed with water, ethanol and then ether and dried at room temperature. This tan solid (293 g.) is added to a mixture of 1500 ml. of water and 1180 ml. of 1 N sodium hydroxide, stirred under nitrogen for one hour, filtered and the filtrate is acidified with concentrated hydrochloric acid. The resulting precipitate is recovered by filtration, washed with water, ethanol, then ether and dried under high vacuum at room temperature giving 205 g. of 4-hydroxy-6-m-nitrobenzamido-2-naphthalenesulfonic acid, sodium salt.

A suspension of 110 g. of 4-hydroxy-6-m-nitrobenzamido-2-naphthalenesulfonic acid, sodium salt is converted to a solution by the addition of sufficient 10 N sodium hydroxide. The solution is filtered and to the filtrate is added 25 g. of 10% palladium-on-carbon catalyst. The mixture is hydrogenated in a 2 liter Parr shaker for 2¾ hours at 25 psi. The reaction mixture is filtered through diatomaceous earth, diluted with water to a volume of 3.5 liters and acidified with concentrated hydrochloric acid. The resulting precipitate is recovered by filtration, washed with water, ethanol, then ether and dried overnight under high vacuum at room temperature, giving the desired product as a grey solid.

EXAMPLE 2

6,6'-[Ureylenebis(m-phenylenecarbonylimino)]bis[4-hydroxy-2-naphthalenesulfonic acid]disodium salt A solution of 200 g. of 6-(m-aminobenzamido)-4-hydroxy-2-naphthalenesulfonic acid, prepared as in Example 1, in a mixture of 3.2 liters of water and 280 ml. of pyridine is warmed to 40° C. and filtered through diatomaceous earth. The filtrate is phosgenated at 18°–28° C. (ice bath cooling) by spraying gaseous phosgene into the mixture until it is strongly acidic. The resulting solid is recovered by filtration and washed with water until the filtrate is almost neutral. The resulting tan-pink paste is dissolved in a mixture of 48 g. of sodium hydroxide in 50 ml. of water at room temperature. The solution is filtered and the filtrate is poured into 12 liters of ethanol:ether (2:1) with vigorous stirring. The solid is recovered by filtration, washed with the ethanol:ether mixture, then ether and air dried giving 331 g. of a yellow powder. This powder is dissolved in 800 ml. of warm water, acidified with 45 ml. of acetic acid and filtered. A 200 ml. portion of water is added, the mixture is heated and then poured into 13.5 liters of ethanol:ether (2:1) with vigorous stirring. The mixture is filtered and the resulting gel is dissolved in 800 ml. of water. The solution is filtered through diatomaceous earth and the filtrate poured into 28.5 liters of ethanol:ether (2:1). The mixture is filtered and the precipitate washed with ethanol:ether (2:1), then ether, dried at room temperature and then dried at 105°–110° C. under high vacuum giving the desired product as a tan-pink powder.

EXAMPLE 3

Amine Precursor
6-(p-Aminobenzamido)-4-hydroxy-2-naphthalenesulfonic acid

A 17.0 g. portion of 6-amino-4-hydroxy-2-naphthalenesulfonic acid is suspended in 175 ml. of water and adjusted to pH 8 with 5 N sodium hydroxide solution. A 12.17 g. portion of sodium acetate trihydrate is added, the mixture is stirred and then filtered. To the filtrate is added 13.67 g. of p-nitrobenzoyl chloride, with vigorous stirring under nitrogen. The mixture is stirred 4 hours. The solid is recovered by filtration, washed with water, ethanol, then ether, slurried in ether and dried in vacuo. This solid is suspended in a mixture of 120 ml. of water and 66 ml. of 1 N sodium hydroxide solution and stirred under nitrogen for one hour. The suspension is acidified with hydrochloric acid and the solid is collected by filtration, washed with water, ethanol, then ether and dried in vacuo, giving 14.5 g. of 4-hydroxy-6-p-nitrobenzamido-2-naphthalenesulfonic acid, sodium salt as a light yellow solid.

A 10.0 g. portion of 4-hydroxy-6-p-nitrobenzamido-2-naphthalenesulfonic acid sodium salt is hydrogenated with palladium on carbon catalyst as described in Example 1 giving 7.6 g. of the desired product as an off-white solid.

EXAMPLE 4

6,6'-[Ureylenebis(p-phenylenecarbonylimino)]bis[4-hydroxy-2-naphthalenesulfonic acid], disodium salt A 6.0 g. portion of 6-(p-aminobenzamido)-4-hydroxy-2-naphthalenesulfonic acid, prepared as in Example 3, is suspended in 96 ml. of water. A 10.4 ml. portion of pyridine is added followed by 5 ml. of 5 N sodium hydroxide causing solution. The mixture is placed in a cold water bath and phosgene gas is passed in with vigorous stirring until the mixture is strongly acidic. The pink solid is collected by filtration, washed with water and then dissolved in a mixture of 4 ml. of 10 N sodium hydroxide and water and filtered. The filtrate is poured into 1200 ml. of ethanol:ether (1:1) with vigorous stirring. The resulting solid is collected by filtration, washed with ethanol:ether (2:1), then ether and dried in vacuo. This solid is dissolved in 20 ml. of water and acidified with 0.7 ml. of acetic acid. Sufficient 5 N sodium hydroxide is added to reach pH 12 and cause solution. A 1200 ml. portion of ethanol:ether (1:1) is added and the solid is collected by filtration, washed with ethanol:ether (2:1), then ether and dried in vacuo. This solid is dissolved in 40 ml. of water and acetic acid is added to pH 6. The resulting solid is collected by filtration, slurried in ethanol, filtered, washed with ethanol, then ether and dried, giving the desired product as 3.15 g. of a light pink solid.

EXAMPLE 5

Amine Precursor
4-(m-Aminobenzamido)-5-hydroxy-1-naphthalenesulfonic acid To a suspension of 50 g. of crude 1-amino-8-naphthol-4-sulfonic acid in 400 ml. of methanol is added sufficient 10 N sodium hydroxide to adjust the pH to 7.5. The resulting solution is filtered through Celite and then twice through a 600 ml. scintered glass funnel coated with magnesol. The filtrate is acidified to pH 3.2. The resulting solid is collected by filtration, washed with methanol, then ether giving 17.8 g. of solid purified 1-amino-8-naphthol-4-sulfonic acid.

To a solution of 10 g. of the above purified amine in 150 ml. of water is added sufficient 1 N NaOH to adjust the pH to 7.7. The solution is filtered and to the filtrate is added 10 g. of sodium acetate trihydrate. This mixture is flushed with a steady stream of argon and then 10 g. of m-nitrobenzoyl chloride is added with vigorous stirring. After 15 minutes, 200 ml. of water are added and stirring is continued for 4 hours. The mixture is filtered and the recovered solid is washed with water, twice with ethanol and then with ether. The solid is then washed with 400 ml. of warm ethanol which is then concentrated giving 5-hydroxy-4-m-nitrobenzamido-1-naphthalenesulfonic acid sodium salt as a bright yellow solid.

A solution of 4.4 g. of the above nitro compound in a mixture of 150 ml. of water and 50 ml. of 1 N sodium hydroxide containing 500 mg. of 10% palladium-on-carbon catalyst is hydrogenated on a Parr apparatus. When hydrogen uptake is complete, the mixture is filtered through Celite and washed with water. The filtrate is acidified to pH 1.5 with concentrated hydrochloric acid. The resulting precipitate is filtered, washed with water, then ethanol and then ether and dried in vacuo at 110° C., giving the desired product as a gray powder.

EXAMPLE 6

4,4'-[Ureylenebis(m-phenylenecarbonylimino)]bis-5-hydroxy-1-naphthalenesulfonic acid, disodium salt To a solution of 2.0 g. of 4-(m-aminobenzamido)-5-hydroxy-1-naphthalenesulfonic acid, prepared as in Example 5, in a mixture of 32 ml. of water and 2.8 ml. of pyridine is added 5.6 ml. of pyridine and more aqueous pyridine to effect solution. The solution is then phosgenated to acidity (pH 3.9), filtered and the solid washed with water until neutral. This solid is dissolved in 12 ml. of 1 N sodium hydroxide and added to 120 ml. of ethanol:ether (2:1). The mixture is concentrated to a residue which is dissolved in 15 ml. of water and 100 ml. of ethanol and 100 ml. of ether are added. The resulting solid is collected by filtration, washed once with 100 ml. of ethanol:ether (1:1), then ether. The solid is dissolved in 15 ml. of water and acidified to pH 6.3 with 0.5 ml. of acetic acid. The solution is warmed, filtered and the filtrate added to 135 ml. of ethanol:ether (2:1). A 45 ml. portion of ether is added and the solid is collected, washed with 50 ml. of ethanol:ether (1:1), then ether and dried in vacuo at 110° C. for 14 hours, giving the desired product.

EXAMPLE 7

6,6'-[Ureylenebis(p-phenylenecarbonylimino)]bis[4-hydroxy-2-naphthalenesulfonic acid]tetrasodium salt To a stirred suspension of one g. of 6,6'-[ureylenebis(p-phenylenecarbonylimino)]bis[4-hydroxy-2-naphthalenesulfonic acid]disodium salt is added 1 N sodium hydroxide until solution occurs (pH 10-12). The solution is then poured into 350 ml. of ethanol:ether (2:1) with vigorous stirring and the precipitate is filtered, washed with ethanol:ether (2:1), ether and dried. The solid is reprecipitated from 5 ml. of water by 300 ml. of ethanol:ether (2:1) to give 300 mg. of product as a brownish solid.

EXAMPLE 8

6,6'-[Ureylenebis(m-phenylenecarbonylimino)]bis[4-hydroxy-2-naphthalenesulfonic acid]tetrasodium salt In the manner described in Example 7, treatment of 6,6'-[ureylenebis(m-phenylenecarbonylimino)]bis[4-hydroxy-2-naphthalenesulfonic acid]disodium salt with sodium hydroxide gives the desired product.

EXAMPLE 9

Amine Precursor
6-(3-Amino-p-toluamido)-4-hydroxy-2-naphthalenesulfonic acid A 17.0 g. portion of 6-amino-4-hydroxy-2-naphthalenesulfonic acid is suspended in 175 ml. of water and adjusted to pH 8 with 5 N sodium hydroxide solution. A 12.17 g. portion of sodium acetate trihydrate is added, the mixture is stirred and then filtered. To the filtrate is added 13.67 g. of 4-methyl-3-nitrobenzoyl chloride with vigorous stirring under nitrogen. The mixture is stirred 4 hours. The solid is recovered by filtration, washed with water, ethanol, then ether, slurried in ether and dried in vacuo. This solid is suspended in 100 ml. of water and 56 ml. of 1 N sodium hydroxide, stirred under nitrogen for one hour, filtered and the filtrate acidified with concentrated hydrochloric acid. The resulting solid is slurried in 800-900 ml. of ethanol, stirred for ½ hour, filtered and the solid is washed with ethanol, then ether and dried in vacuo giving 11.2 g. of 4-hydroxy-6-(3-nitro-p-toluamido)-2-naphthalenesulfonic acid sodium salt.

A 10.0 g. portion of 4-hydroxy-6-(3-nitro-p-toluamido)-2-naphthalenesulfonic acid sodium salt is suspended in 200 ml. of water and 10 N sodium hydroxide solution is added until solution is complete (pH 11). The mixture is filtered and to the filtrate is added 2.5 g. of 10% palladium-on-carbon. The mixture is hydrogenated in a Parr shaker until no additional hydrogen is taken up, filtered through diatomaceous earth and washed with water. The combined filtrate and washing is acidified with hydrochloric acid and the solid is collected by filtration, washed with water, ethanol, then ether and dried in a pistol giving the desired product as 7.5 g. of an off-white solid.

EXAMPLE 10

6,6'-[Ureylenebis(4-methyl-3,1-phenylene)carbonylimino]bis[4-hydroxy-2-naphthalenesulfonic acid]disodium salt A mixture comprising 6.0 g. of 6-(3-amino-p-toluamido)-4-hydroxy-2-naphthalenesulfonic acid, prepared as in Example 9, 15 ml. of pyridine, 3 ml. of 5 N sodium hydroxide and 92 ml. of water is warmed to produce solution, filtered and the filtrate is phosgenated in a cold water bath with gaseous phosgene, until strongly acidic and until thin layer chromatography shows no more starting amine. The solid is recovered by filtration and washed with water. This paste is dissolved in a mixture of 4 ml. of 10 N sodium hydroxide and 5 ml. of water and poured into 1200 ml. of ethanol:ether (1:1). The solid is collected by filtration, washed with ethanol:ether (2:1) and dried in vacuo. The solid is dissolved in 20 ml. of water and acidified with 0.7 ml. of acetic acid. A 10 ml. portion of water is added and the mixture is heated to solution on a steam bath and then poured into 750 ml. of ethanol:ether (2:1), with vigorous stirring. The resulting precipitate is collected by filtration, washed with ethanol:ether (2:1) and dried in a pistol, giving the desired product as 3.88 g. of a light pink solid.

EXAMPLE 11

Amine Precursor
6-(4-Amino-m-toluamido)-4-hydroxy-2-naphthalenesulfonic acid

In the manner described in Example 9, reaction of 7-amino-4-hydroxy-1-naphthalenesulfonic acid with 4-methyl-3-nitrobenzoyl chloride and sodium acetate in water gives 4-hydroxy-6-(4-nitro-m-toluamido)-2-naphthalenesulfonic acid sodium salt as a yellow oil. This oil is then catalytically reduced as described in Example 9 to give the desired product as a white solid.

EXAMPLE 12

6,6'-[Ureylenebis(3-methyl-4,1-phenylene)carbonylimino]bis[4-hydroxy-2-naphthalenesulfonic acid]disodium salt In the manner described in Example 10, reaction of 6-(4-amino-m-toluamido)-4-hydroxy-2-naphthalenesulfonic acid with phosgene in pyridine and water gives the desired product as a light pink solid.

EXAMPLE 13

Preparation of Compressed Tablet

| Ingredient | mg/Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 14

Preparation of Compressed Tablet-Sustained Action

| Ingredient | mg/Tablet |
|---|---|
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Collagenase inhibitor plus aluminum sulfate yields aluminum collagenase inhibitor. Collagenase inhibitor content in aluminum lake ranges from 5–30%.

EXAMPLE 15

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 16

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 17

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 18

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 19

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 20

Preparation of Injectable Oil

| Ingredient | % W/V |
|---|---|
| Active Compound | 0.05–5 |
| Benzyl Alcohol | 1.5 |

| -continued | |
|---|---|
| Ingredient | % W/V |
| Sesame Oil qs ad | 100.0 |

EXAMPLE 21

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 22

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 23

Preparation of Dental Paste

| Ingredient | % W/W |
|---|---|
| Active Compound | 0.05–5 |
| Zinc Oxide | 15 |
| Polyethylene Glycol 4000 USP | 50 |
| Distilled Water qs | 100 |

EXAMPLE 24

Preparation of Dental Ointment

| Ingredient | % W/W |
|---|---|
| Active Compound | 0.05–5 |
| Petrolatum, White USP qs | 100 |

EXAMPLE 25

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 26

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 27

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 28

Preparation of Spray Lotion (non-Aerosol)

| Ingredient | % W/W |
|---|---|
| Active Compound | 0.05–5 |
| Isopropyl Myristate | 20 |
| Alcohol (Denatured) qs | 100 |

EXAMPLE 29

Preparation of Buccal Tablet

| Ingredient | g/Tablet |
|---|---|
| Active Ingredient | 0.00325 |
| 6x Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 30

Preparation of Lozenge

| Ingredient | g/Lozenge |
|---|---|
| Active Ingredient | 0.0140 |
| Kompact ® Sugar (Sucrest Co.) | 0.7138 |
| 6x Sugar | 0.4802 |
| Sorbitol (USP Crystailine) | 0.1038 |
| Flavor | 0.0840 |
| Magnesium Stearate | 0.0021 |
| Dye | qs |
| Stearic Acid | 0.0021 |
| | 1.4000 |

The ingredients are compressed into 5/8" flat based lozenge tooling. Other shapes may also be utilized.

EXAMPLE 31

Preparation of Gelled Vehicles

| Ingredient | % W/W |
|---|---|
| Active Compound | 9–11 |
| Sodium Chloride | 0.9–1.2 |
| Buffer and Flavor qs | – |
| Purified Water qs ad | 100 |
| | |
| Active Compound | 0.005–9 |
| Sodium Alginate | 0.5–2 |
| Buffer and Flavor qs | — |
| Purified Water qs ad | 100 |
| | |
| Active Compound | 0.005–9 |
| Hydroxypropyl Cellulose | 0.5–2 |
| Buffer and Flavor qs | — |
| Purified Water qs ad | 100 |
| | |
| Active Compound | 0.005–9 |
| Guar Gum | 0.5–2 |
| Buffer and Flavor qs | — |
| Purified Water qs ad | 100 |

EXAMPLE 32

Preparation of Oral Mouth Rinse

| Ingredient | % W/V |
|---|---|
| Active Compound | 0.05–20 |
| Alcohol U.S.P. | 0–20 |
| Sorbitol | 1–30 |
| Buffer and Flavor qs | — |
| Polysorbate 80 | 0.1–3 |
| Cetyl Pyridinium Chloride | 0.025–0.20 |
| Purified Water qs ad | 100 |

EXAMPLE 33

Preparation of Tooth Paste

| Ingredient | % W/W |
|---|---|
| Active Compound | 0.05–15 |
| Glycerin | 5–15 |
| Sorbitol | 5–15 |
| Sodium Carboxymethylcellulose | 0.5–2 |
| Magnesium Aluminum Silicate | 0.1–1 |
| Carrageenin | 0.25–2 |
| Preservative qs | — |
| Sodium Lauryl Sulfate | 0.1–3 |
| Calcium Carbonate | 25–45 |
| Flavor qs | — |
| Purified Water qs ad | 100 |

EXAMPLE 34

Preparation of Dental Paste

| Ingredient | % W/W |
|---|---|
| Active Compound | 0.05–20 |
| Carboxymethylcellulose | 5–20 |
| Pectin | 5–20 |
| Plastibase ® | 20–70 |
| Gelatin | 5–20 |

EXAMPLE 35

Preparation of Dental Ointment

| Ingredient | % W/W |
|---|---|
| Active Compound | 0.05–20 |
| Polyethylene Glycol 4000 | 50–80 |
| Polyethylene Glycol 400 | 10–40 |

EXAMPLE 36

Preparation of Dental Powder for Brushing or for Use in Water Spray (e.g. Water Pik ®)

| Ingredient | % W/W |
|---|---|
| Active Compound | 0.05–10 |
| Flavor qs | — |
| Wetting Agents qs | — |
| Dextrin qs ad | 100 |

EXAMPLE 37

Preparation of Stick for Application to Gums

| Ingredient | % W/W |
|---|---|
| Active Compound | 0.05–10 |
| Glycerin | 5–10 |
| Propylene Glycol | 40–80 |
| Sodium Stearate | 6–10 |
| Flavor qs | — |
| Water | 0–10 |

EXAMPLE 38

Preparation of Periodontal Packing Paste

Paste Part A

| Ingredient | % W/W |
|---|---|
| Active compound | 0.05–20 |
| Caprylic acid | 9.0 |
| Lauric acid | 27.0 |
| Ethylcellulose (100 cps.) | 2.0 |
| Polypale resin* | 39.0 |
| Gum elemi | 4.0 |
| Brominol** | 4.0 |
| Mica (powdered) | 7.5 |
| Chlorothymol | 1.0 |
| Zinc acetate | 2.0 |
| Bay oil (essential oil) | 1.0 |
| Ethanol | 1.5 |

*Partially polymerized rosin (i.e. modified eoain)
**Brominated olive oil

Paste Part B

| Ingredient | % W/W |
|---|---|
| Magnesium oxide | 43.0 |
| Zinc oxide | 21.0 |
| Calcium hydroxide | 3.5 |
| Copper oxide | 2.0 |
| Mineral oil, Heavy | 26.0 |
| Rosin oil | 3.0 |
| Chlorothymol | 1.4 |
| Cumarin (flavor) | 0.1 |

When equal parts of A and B are mixed together at 25° C. a hard mass is formed in about 3 minutes.

EXAMPLE 39

Preparation of Periodontal Packing Paste

| Part A (Powder) | |
|---|---|
| Ingredient | % W/W |
| Active compound | 0.05–20 |
| Canada Balsam, Neutral | 8.5 |
| Rosin NF | 8.5 |
| Calcium hydroxide | 34.4 |
| Zinc oxide U.S.P. | 46.6 |
| Part B (Liquid Hardener) | |
| Eugenol | 85.0 |
| Turpentine oil, rectified | 15.0 |

A mixture of three drops of Part B added to 130 mg. of Part A produces a hard mass in about 2–3 minutes at 30° C.

The compounds of this invention may be administered internally to a warm-blooded animal to inhibit connective tissue destruction or collagenase, such inhibition being useful in the amelioration or prevention of those reactions causing connective tissue damage. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 1.5 mg/kg to about 100 mg/kg of body weight of animal per day. The usual daily dosage for a 70 kg subject may vary from about 100 mg to about 3.5 g. Unit doses can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanolamine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The compounds of the present invention may also be administered topically in the form of ointments, creams, lotions and the like, suitable for the treatment of connective tissue dependent dermatological disorders.

Moreover, the compounds of the present invention may be administered in the form of dental pastes, ointments, buccal tablets and other compositions suitable for application periodontally for the treatment of periodontitis and related diseases of the oral cavity.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such as active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The inhibiting activity of representative compounds of the invention on the destruction of connective tissue has been demonstrated by one or more of the following identified tests: (i) Collagenase Assay, Test Code 006—This test measures the ability of human skin fibroblast collagenase to degrade radiolabeled native collagen fibrils. An active inhibitor inhibits the degradation of the collagen fibril; (ii) Crevicular Fluid Assay—In an

TABLE III

| Leukocyte Neutral Proteases Inhibitor Assay | | |
|---|---|---|
| Concentration of 6'6'-[urey-lenebis(m-phenylenecarbonyl-imino)]bis(4-hydroxy-2-naphthalenesulfonic acid)disodium salt in mcg./ml. | Percent Inhibition of Neutral Protease Activity | |
|  | $^3H$ | $^{35}S$ |
| 0 | 0 | 0 |
| 0.5 | 0 | 0 |
| 1.0 | 17 | 31 |
| 2.0 | 21 | 37 |
| 5.0 | 47 | 74 |
| 10.0 | 63 | 91 |

Evidence seems to indicate that certain compounds tested interact by binding with the substrate, e.g., fibrillar collagen, and the resulting complex is then not readily susceptible to degradation by fibroblast collagenase. Evidence supporting this view has been obtained from the following experiments.

Fibrillar collagen was preincubated with the test compounds at 37° C. for 90 to 120 minutes. After this preincubation, the fibrillar collagen was pelleted by centrifugation and unbound test compound was removed by aspiration. Addition of collagenase to these pelleted mixtures resulted in a decreased degradation of collagen when compared to the preincubation mixtures that had not contained test compound. Therefore, the compounds protect preexisting collagen of the oral tissue from degradation by collagenase.

The test compounds are able to inhibit the degradation of collagen of gingival tissue. Dried pieces of human gingiva were incubated at 37° C. for 36 hours with fibroblast collagenase and leukocyte neutral protease in the presence of test compound (30 and 50 μg./ml.). Antibiotics were present to prevent bacterial growth. After incubation, the residual tissue was hydrolyzed in 6 N hydrochloric acid and the hydroxyproline content (collagen) was determined. When collagenase and neutral protease were added to human gingiva, approximately 100 μg of collagen/mg. dry tissue was digested. If the test compound was present, degradation of gingival collagen was inhibited. Results of this experiment are shown in Table IV.

TABLE IV

| Enzymatic Degradation of Collagen of Human Gingiva | |
|---|---|
| Conditions | mcg. of Collagen degraded per mg. of dry gingiva |
| Collagenase, neutral proteases | 102.3 |
| Collagenase, neutral proteases plus 30 mcg./ml. of 6,6'-[urey-lenebis(m-phenylenecarbonyl-imino)]bis(4-hydroxy-2-naphthalenesulfonic acid)disodium salt | 60.4 |
| Collagenase, neutral proteases plus 50 mcg./ml. of 6,6'-[urey-lenebis(m-phenylenecarbonyl-imino)]bis(4-hydroxy-2-naphthalenesulfonic acid)disodium salt | 27.4 |

I claim:

1. A compound selected from those of the formula:

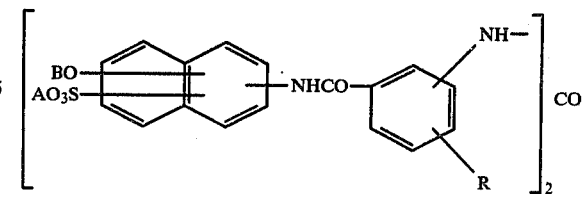

wherein A is hydrogen or a pharmaceutically acceptable salt cation; B is hydrogen, lower ($C_1$–$C_6$) alkanoyl or alkali metal; and R is hydrogen.

2. A compound according to claim 1 of the formula:

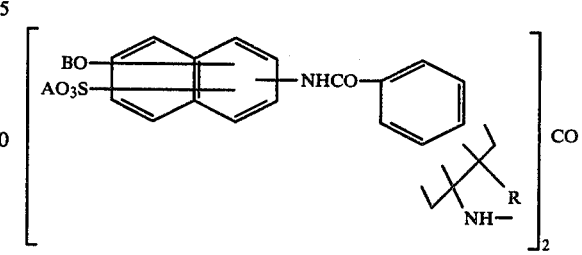

wherein A is hydrogen or a pharmaceutically acceptable salt cation; B is hydrogen, lower ($C_1$–$C_6$) alkanoyl or alkali metal; and R is hydrogen.

3. A compound according to claim 1 of the formula:

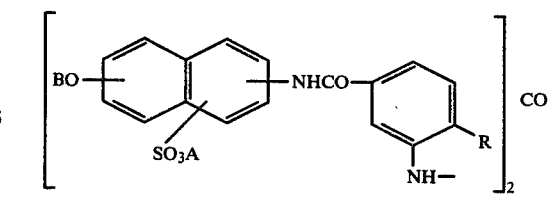

wherein A is hydrogen or a pharmaceutically acceptable salt cation; B is hydrogen, lower ($C_1$–$C_6$) alkanoyl or alkali metal; and R is hydrogen.

4. A compound according to claim 1 of the formula:

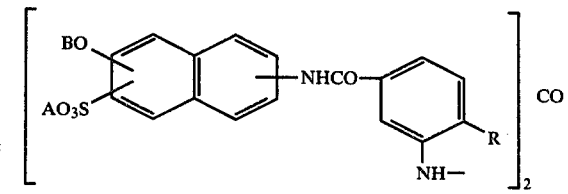

wherein A is hydrogen or a pharmaceutically acceptable salt cation; B is hydrogen, lower ($C_1$–$C_6$) alkanoyl or alkali metal; and R is hydrogen.

5. A compound according to claim 1, 6,6'-[ureylenebis(m-phenylenecarbonylimino)]bis[4-hydroxy-2-naphthalenesulfonic acid]disodium salt.

6. A compound according to claim 1, 6,6'-[ureylenebis(p-phenylenecarbonylimino)]bis[4-hydroxy-2-naphthalenesulfonic acid], disodium salt.

7. A compound according to claim 1, 4,4'-[ureylenebis(m-phenylenecarbonylimino)]bis[-5-hydroxy-1-naphthalenesulfonic acid], disodium salt.

8. A compound according to claim 1, 6,6'-[ureylenebis(p-phenylenecarbonylimino)]bis[4-hydroxy-2-naphthalenesulfonic acid]tetrasodium salt.

9. A compound according to claim 1, 6,6'-[ureylenebis(m-phenylenecarbonylimino)]bis[4-hydroxy-2-naphthalenesulfonic acid]tetrasodium salt.

* * * * * analogous test, collagenase present in the crevicular fluid of inflamed gingival tissue was used to measure its ability to degrade radiolabeled native collagen fibrils. An active inhibitor would inhibit the degradation of the collagen fibril; (iii) Leukocyte Neutral Proteases Inhibitor Assay—This test measures the ability of neutral proteases derived from human leukocytes to degrade radiolabeled proteoglycans entrapped in polyacrylamide beads. An active inhibitor inhibits the degradation of proteoglycans.

(i) Collagenase Assay—Test Code 006

Collagenase assays were performed by a modification of the method of Harper, et al., Biochem., 10, 3035 (1971). In a typical assay (total volume of 0.45 ml.), 100 μl. of the activated enzyme was added to the $^{14}C$-labeled collagen fibrils (250 μl.) followed by 100 μl. of 50 mM cacodylate, pH 7.4, containing 5 mM calcium chloride. After incubation at 37° C. for 16 hours, the tubes were centrifuged in a Beckman microfuge for five minutes at full speed. An aliquot (200 μl.) of the supernatant, representing collagenase digestion products of the fibril, was assayed for radioactivity. The effect of the test compound on collagen degradation by collagenase was examined as follows:

Varying concentrations of the test compound (in distilled water) were added to the assay tubes containing active collagenase (total volume 450 μl.) and after 16 hours the amount of radioactivity in the supernatant was determined. Appropriate blanks and trypsin controls were run in parallel.

Table I shows that representative compounds of the invention possess collagenase inhibitory activity. The activities are expressed as % inhibition (lowering) of collagenase activity, e.g. based on the 0% value for the enzyme control.

TABLE I

Biological Activities
(test conc.: 30 μg./ml.)
*Dimethylacetamide

| Compound | % Inhibition of Collagenase |
|---|---|
| 6,6'-[Ureylenebis(4-methyl-3,1-phenylene)carbonylimino]bis-[4-hydroxy-2-naphthalenesulfonic acid]disodium salt | 73% |
| 6,6'-[Ureylenebis(p-phenylenecarbonylimino)]bis[4-hydroxy-2-naphthalenesulfonic acid]disodium salt | 86% |
| | 96% (DMA)* |
| tetrasodium salt | 95%, 92% |
| 6,6'-[Ureylenebis(3,1-phenylenecarbonylimino)]bis[4-hydroxy-2-naphthalenesulfonic acid]disodium salt | 82%, 69% |
| | 81% (DMA)* |
| tetrasodium salt | 82%, 81% |
| 4,4-[Ureylenebis(3,1-phenylenecarbonylimino)]bis[5-hydroxy-1-naphthalenesulfonic acid]disodium salt | 84%, 69% |
| | 60%, 55% |

(ii) Crevicular Fluid Assay

Effect of Test Compounds on Gingival Crevicular Fluid Collagenase

Since studes by Golub, et al., Dental Res., 55, 1049 (1976) have shown that the crevicular collagenase plays a major role in the degradation of collagen in periodontal tissue, the effect of test compounds on collagen degradation by this system was examined. A volunteer with diagnosed periodontal disease was used. The area around the gums was dried and a sterile filter paper strip (2×13 mm., Harco Electronics, Ltd., Winnipeg, Canada) was inserted into the gingival crevice with the aid of a forceps. The gingival crevicular fluid that had accumulated in the periodontal pocket was absorbed by the filter paper strip in approximately one minute. After one minute, the filter paper strip was removed and the volume of the gingival crevicular fluid was measured with the aid of the Periotron (Harco Electronics, Ltd., Winnipeg, Canada). The volume of the fluid gathered from the crevice by the filter paper strip is translated by a unique transducer onto a digital readout screen. The relative wetness of the paper strip affects the flow of an electrical current. Hence, the greater the volume of the fluid (the greater the paper's capacity to conduct the current) the higher the readout on the digital meter. After reading on the meter, 1 μl. of trypsin (1.5 μg./ml.) was added to the filter paper (to activate any latent collagenase present) and after five minutes at room temperature 1 μl. of aprotinin was added. The filter strip was layered on top of $^{14}C$-collagen fiibrils (250 μl. gel volume). Two hundred μl. of 50 mM cacodylate buffer, pH 7.4, containing 5 mM calcium chloride was added (final volume 450 μl.) and the tubes were incubated at 37° C. for approximately 90 hours. Some reaction mixtures contained test compounds at a final concentration of 30 μg./ml. The tubes were centrifuged as described above and a 200 μl. aliquot of the clear supernatant was assayed for radioactivity.

The results of this test on a representative compound of this invention are given in Table II.

TABLE II

| Compound | cpm Collagen Degraded/Unit Periotron Reading |
|---|---|
| Diseased crevicular fluid | 66 ± 9 |
| Diseased crevicular fluid + 30 mcg./ml. of 6,6'-[ureylenebis(m-phenylenecarbonylimino)]bis[4-hydroxy-2-naphthalenesulfonic acid]disodium salt | 16 ± 6* |

*Statistically significant p<0.0005

(iii) Leukocyte Neutral Proteases Inhibitor Assay

Assays of Leukocyte Neutral Proteases Using $^3H/^{35}S$ Labeled Proteoglycans

This assay system contained (total volume of 1 ml.) 60 mM Tris-Cl, pH 7.4; 2.5 mM calcium chloride; 2.5 mM magnesium chloride; 2 mg. (dry weight) of polyacrylamide beads entrapped with labeled proteoglycans, and an aliquot of the leukocyte neutral protease preparation. The reaction mixture was incubated at 37° C. for 30 minutes in a shaking water bath. The reaction was terminated by the addition of 0.2 ml. of 5% HCl (v/v). After five minutes at room temperature, the mixture was centrifuged and the clear supernatant (0.6 ml.) was assayed for radioactivity. To determine the effect of the test compounds on degradation of proteoglycans by neutral proteases, various concentrations of the compounds were added to the reaction mixture. Appropriate blanks were included. The results of this test appear in Table III.